(12) United States Patent
Roberts et al.

(10) Patent No.: US 6,825,933 B2
(45) Date of Patent: Nov. 30, 2004

(54) COMPUTER-IMPLEMENTED REFLECTANCE SYSTEM AND METHOD FOR NON-DESTRUCTIVE LOW DOSE ION IMPLANTATION MONITORING

(75) Inventors: Jeff Roberts, Sunnyvale, CA (US); Abdul Rahim Forouhi, Cupertino, CA (US)

(73) Assignee: N&K Technology, Inc., Santa Clara, CA (US)

( * ) Notice: Subject to any disclaimer, the term of this patent is extended or adjusted under 35 U.S.C. 154(b) by 68 days.

(21) Appl. No.: 10/165,771

(22) Filed: Jun. 7, 2002

(65) Prior Publication Data

US 2003/0227630 A1 Dec. 11, 2003

(51) Int. Cl.[7] .............................................. G01N 21/55
(52) U.S. Cl. ..................................................... 356/445
(58) Field of Search ................................ 356/445–448, 356/369, 364, 368, 381, 382, 367; 250/225

(56) References Cited

U.S. PATENT DOCUMENTS

| | | | |
|---|---|---|---|
| 4,352,017 A | 9/1982 | Duffy et al. ............. | 250/358.1 |
| 4,513,384 A | 4/1985 | Rosencwaig ................ | 364/563 |
| 4,750,822 A | 6/1988 | Rosencwaig et al. ....... | 356/445 |
| 4,766,317 A | 8/1988 | Harbeke et al. ......... | 250/358.1 |
| 4,854,710 A | 8/1989 | Opsal et al. ................ | 356/432 |
| 4,905,170 A | 2/1990 | Forouhi et al. ............. | 364/556 |
| 4,952,063 A | 8/1990 | Opsal et al. ................ | 356/432 |
| 5,007,741 A | 4/1991 | Carver et al. ............... | 356/448 |
| 5,042,952 A | 8/1991 | Opsal et al. ................ | 356/432 |
| 5,074,669 A | 12/1991 | Opsal ......................... | 356/445 |
| 5,365,334 A | 11/1994 | Bottka ........................ | 356/326 |
| 5,396,080 A | 3/1995 | Hannotiau et al. .......... | 250/560 |
| 5,564,830 A | 10/1996 | Bobel et al. ................ | 374/126 |

(List continued on next page.)

OTHER PUBLICATIONS

"Low–Dose Ion Implant Monitoring Methods," Therma–Wave, Inc. Technical Note TP–01, Apr., 1986, pp. 1–4.

A. Yu. Zdobnikov et al. "Use of Infrared Reflection Spectra to Investigate Ion–Doped Layers of INSB Crystals," Soviet Physics–Crystallography, vol. 28, No. 5, P6615–16, Publication Date Sep.–Oct. 1983.

G. A. Shifrin et al. "Effect of Ion–Implantation Damage on the Optical Reflection Spectrum of Gallium Arsenide," vol. 17, No. 7, p. 274–6, Publication Date Oct. 1, 1970.

Jeff f. Young et al. "A Simple, Non–Destructive Optical Technique to Characterize Ion–Implanted Semiconductor Vafers," Mat. Res. Soc. Sump. Proc. vol. 52, 1986, Materials Research Society, pp 83–90.

W. A. Keenan et al. "Advances in Sheet Resistance Maeasurements for Ion Impant Monitoring," Solid Stae Tech., Jun. 1985, pp. 143–148.

J. R. Golin et al. "Advanced Methods of Ion Implant Monitoring Using Optical Dosimetry," Solid State Tech, Jun. 1985, pp. 155–163.

(List continued on next page.)

*Primary Examiner*—Michael P. Stafira
(74) *Attorney, Agent, or Firm*—Lumen Intellectual Property Services, Inc.

(57) ABSTRACT

Embodied in a reflectance system capable of providing high resolution, repeatable, efficient, and accurate reflectance measurements of a silicon or silicon-oxide wafer at all wavelengths, the present invention, including an inventive and useful software tool with user interface, provides a solution to monitor non-destructively low dose ion implantation without potentially suffering from undesirable annealing effect. The computer-implemented method disclosed herein determines a reflectance change index that correlates to the ion dose. The reflectance change index is determined based on an absolute value of reflectance changes over the entire measured spectra. The reflectance changes are determined based on non-implanted and implanted reflectance measurements of the wafer respectively obtained at each of the wavelengths.

38 Claims, 7 Drawing Sheets

U.S. PATENT DOCUMENTS

| | | | | |
|---|---|---|---|---|
| 5,595,916 | A | | 1/1997 | Fujimura et al. ............... 437/8 |
| 5,706,094 | A | * | 1/1998 | Maris ......................... 356/432 |
| 5,796,484 | A | | 8/1998 | Honma et al. .............. 356/371 |
| 5,825,498 | A | | 10/1998 | Thakur et al. .............. 356/394 |
| 5,835,225 | A | | 11/1998 | Thakur ....................... 356/381 |
| 5,850,288 | A | | 12/1998 | Honma et al. .............. 356/371 |
| 5,864,633 | A | | 1/1999 | Opsal et al. ................ 382/141 |
| 5,880,831 | A | | 3/1999 | Buermann et al. .......... 356/319 |
| 6,008,906 | A | | 12/1999 | Maris ......................... 356/432 |
| 6,049,220 | A | | 4/2000 | Borden et al. .............. 324/765 |
| 6,141,103 | A | * | 10/2000 | Pinaton et al. .............. 356/369 |
| 6,195,163 | B1 | | 2/2001 | Thakur et al. ............ 3556/371 |
| 6,268,916 | B1 | * | 7/2001 | Lee et al. ................... 356/369 |
| 6,275,292 | B1 | | 8/2001 | Thakur et al. .............. 356/371 |
| 6,284,552 | B1 | | 9/2001 | Yamagata et al. ............ 438/14 |
| 6,323,951 | B1 | | 11/2001 | Borden et al. .............. 356/502 |
| 6,327,040 | B2 | | 12/2001 | Thakur et al. .............. 356/600 |
| 6,462,817 | B1 | * | 10/2002 | Strocchia-Rivera ......... 356/369 |
| 2002/0080356 | A1 | * | 6/2002 | McMillen et al. .......... 356/445 |
| 2003/0137668 | A1 | * | 7/2003 | Opsal et al. ................ 356/432 |

OTHER PUBLICATIONS

P. S. Krishnaprasad et al. "A Wavelet Approach to Wafer Temperature Measurement Via Diffuse Reflectance Spectroscopy," No. TR 96–61, Year: 1996, pp. 1–12.

Michael I. Current and C. B. Yarling (ed,) "Materials and Process Characterization of Ion Implantation," Ion Beam Press, Austin, Texas, $1^{st}$ Edition, 1997, p. 8–12.

Application–Ion Implantation Monitoring, "Application of the Thermal Wave Technique for Ion Implantation Monitoring," retrieved on Apr. 16, 2002. Retrieved from the internet: < URL: http://www.thermawave.com/apps/implant.htm>.

Application of Contactless Sheet Resistance Probes, p. 2, retrieved on Apr. 16, 2002. Retrieved from the internet: <URL: http://www.lehigton.com/fabtech/page2.html>.

Robin Sarah Ticky et al. "Annealing of Ultra–Shallow Implanted Junctions Using Arc–Lamp Technology: Achieving the 90 NM Node," Last Modified Apr. 9, 2002, retrieved on May 2, 2002. Retrieved from the internet: <URL: http://www.vortek.com/papers/>.

B. A. Young et al., "Measurement of $T_C$ Suppression in Tungstem Using Magnetic Impurities," Journal of Applied Physics, vol. 86, No. 12, Dec. 15, 1999.

* cited by examiner

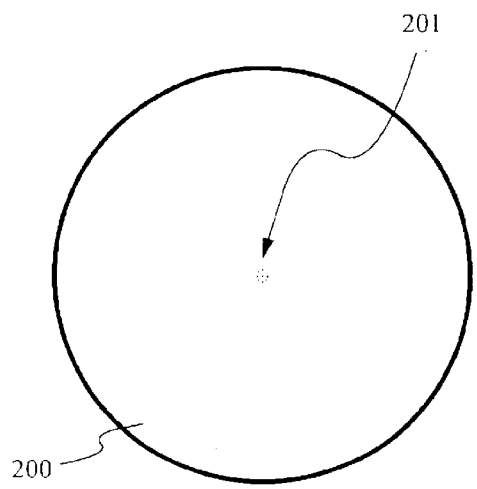 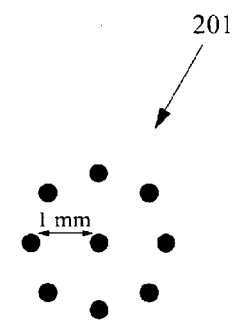
FIG. 2A      FIG. 2B
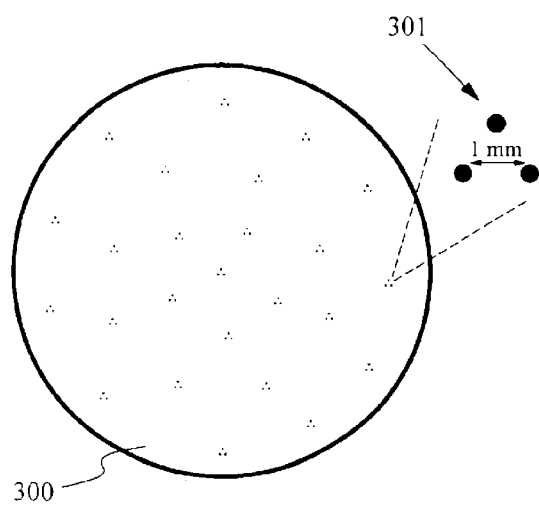 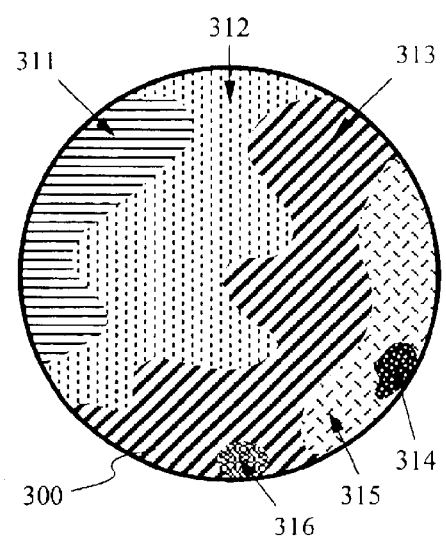
FIG. 3A      FIG. 3B

COMPUTER-IMPLEMENTED REFLECTANCE SYSTEM AND METHOD FOR NON-DESTRUCTIVE LOW DOSE ION IMPLANTATION MONITORING

BACKGROUND OF THE INVENTION

1. Field of the Invention

This invention relates generally to low dose ion implantation monitoring. More particularly, this invention relates to a computer-implemented reflectance system and method for associating absolute values of reflectance changes over the entire measured spectra to doses of ions implanted in a semiconductor wafer for high resolution ion implantation monitoring in a non-destructive, efficient, accurate, and repeatable manner.

2. Description of the Related Art

In the semiconductor manufacturing industry, certain materials are often doped with impurities to change their properties such as electrical or physical properties during different stages of the semiconductor manufacturing process. These materials may include silicon, germanium, or gallium arsenide. The impurities, i.e., dopants or doping agents, such as B, P, Ga, Ge, F, Si, B11, BF2, Sb, In, As, and H, can be diffused or implanted into the materials. The diffusion process is useful for large-scale applications. The ion beam implantation is presently being utilized in small-scale electrostatic processes.

For different purposes, implant doses may vary from about $10^{10}$ ions/cm$^2$ to about $10^{18}$ ions/cm$^2$. During an ion implantation process, ions of a doping agent enter a semiconductor material and collide with atoms of the material, causing displacements of the atoms. As a result, the material is damaged or modified in regions implanted, i.e., doped, with the ions. A common practice in the art to remove some of the damage to the crystalline structure is by thermally annealing the material, although part of the material may become amorphous rather than crystalline with a sufficiently high dose.

As is well known in the art, because of the small dimensions and narrow dose tolerances of the devices being created, it is critically important to accurately monitor and/or characterize the ion implant doses. The monitored result or characterization can also be used, for example, to evaluate, analyze, and characterize the electrical and/or physical properties of the semiconductor device and/or material for purposes such as flaw testing.

There are several known methods for monitoring ion implant doses, including sheet resistance based methods and thermal wave based methods. The sheet resistance based methods include, for example, single implant sheet resistance method and double implant sheet resistance method.

The single implant sheet resistance method uses a 4-point probe to measure the sheet resistance of specially prepared and treated silicon test wafers after implantation and activation. Most technologies do not rely on this method for low dose monitoring because of the fundamental difficulties in measuring reproducible sheet resistances in the regime of 100,000 ohm/sq. or more.

The double implant sheet resistance method measures the change in 4-point probe sheet resistance of a previously implanted and activated silicon test wafer that is subsequently damaged from a low dose (second) ion implantation. This method suffers from considerable process complexity that causes major wafer-to-wafer reproducibility problems.

The sheet resistance based methods are well known in the art and thus are not further described herein for brevity. For an exemplary teaching on the sheet resistance based methods, readers are referred to "Advances in Sheet Resistance Measurements for Ion Implant Monitoring" by W. A. Keenan et al., Solid State Tech., June 1985, pp. 143–148.

The thermal wave based methods are currently being used in the semiconductor manufacturing process. By analyzing thermal waves generated in an implanted silicon wafer, this type of methods provides a rather non-destructive way of monitoring ion implants in the wafer. The thermal wave methods are based on the effect that damage to the silicon crystal lattice that takes place during ion implantation increases the thermal wave signal above that of the non-implanted silicon wafer. Exemplary teachings on thermal wave systems and methods can be found in the following U.S. patents: U.S. Pat. No. 4,513,384, titled "THIN FILM THICKNESS MEASUREMENTS AND DEPTH PROFILING UTILIZING A THERMAL WAVE DETECTION SYSTEM" and U.S. Pat. No. 4,750,822, titled "METHOD AND APPARATUS FOR OPTICALLY DETECTING SURFACE STATES IN MATERIALS," both of which are issued to Rosencwaig and assigned to Therma-Wave, Inc. of Fremont, Calif., U.S.A.; U.S. Pat. Nos. 4,854,710, 4,952,063, and 5,042,952, titled "METHOD AND APPARATUS FOR EVALUATING SURFACE AND SUBSURFACE FEATURES IN A SEMICONDUCTOR" and U.S. Pat. No. 5,074,669, titled "METHOD AND APPARATUS FOR EVALUATING ION IMPLANT DOSAGE LEVELS IN SEMICONDUCTORS," all of which are issued to Opsal et al. and assigned to Therma-Wave, Inc. of Fremont, Calif., U.S.A.

The thermal wave based optical systems and methods utilize laser-induced modulation of the optical reflectance. As such, a thermal wave signal is a modulated reflectance signal. Values of the thermal wave signal thus vary depending upon the type of the doping agent (dopant) used. For example, the thermal wave signal values range from 200 to 10,000 for boron (B) ions and from 500 to 100,000 for heavier ions such as phosphorus (P) and arsenic (As) ions. The thermal wave signal and dose for P and As ion implants have a somewhat one to one correlation at low dose ranges of 1E10 to 3E14 ions/cm$^2$. The thermal wave signal correlates well with dose and threshold voltage at low dose ranges of 1E11 to 1E12 ions/cm$^2$.

It is important to note, although the thermal wave signal depends primarily on implant dose, it can be influenced, to a smaller degree, by other implant parameters such as beam energy, beam current and wafer temperature. According to "Materials and Process Characterization of Ion Implantation" edited by Michael I. Current and C. B. Yarling and published by Ion Beam Press, Autstin, Tex., USA, 1997, pp. 8–12, which is hereby incorporated by reference, the thermal wave sensitivity varies for different penetration depths of ions in silicon. It is also sensitive to channeling and various scanning effects.

Additionally, as discussed heretofore, thermally annealing the wafer may remove some of the undesirable damage to the crystalline structure. This annealing process has the potential to also remove some of the desirable modification thereof, i.e., regions of the crystalline structure modified (patterned) with ion implants, thereby causing an undesirable annealing effect. This undesirable annealing effect may potentially be a problem in thermal wave based systems as semiconductor technologies continue to scale because of the 100% intensity modulated laser beam commonly utilized in these systems. That is, some of the intended modification to the crystalline structure may be undesirably removed by the localized heating of the material, rendering the non-destructiveness of these thermal wave based systems questionable.

The concern of undesirable annealing effect generally applies to dose measurement monitoring systems where wafer temperature is increased during the measuring and/or monitoring process. For example, in U.S. Pat. No. 6,268,916, titled "SYSTEM FOR NON-DESTRUCTIVE MEASUREMENT OF SAMPLES," issued to Lee et al., and assigned to Kla-Tencor Corporation of San Jose, Calif., U.S.A., Lee et al. disclosed how to use heat dissipation characteristics of a semiconductor wafer to measure physical properties thereof. The surface temperature of an area of the semiconductor wafer is increased by heat, which is generated by a pump beam produced by an infrared laser. When the wafer has been doped with a dopant, the heat dissipation characteristics of the wafer at the surface area are dependent upon the dose and the implant profile in the damaged layers in the wafer. The heat dissipation characteristics, in turn, determine the change in the temperature of the wafer surface and the change in the complex index of refraction of the surface. The ellipsometer system disclosed by Lee et al. provides a probe beam for interrogating such changes.

Other non-destructive optical systems and methods that do not rely on the thermal wave principle have been developed for use in measuring, monitoring, analyzing, and characterizing semiconductor substrate materials, particular the surface thereof, and the thin films deposited on the surface of the substrate materials. For example, U.S. Pat. No. 4,766,317, titled "OPTICAL REFLECTANCE METHOD OF EXAMINING A SIMOX ARTICLE," issued to Harbeke et al., and assigned to General Electric Company of Schenectady, N.Y., U.S.A., disclosed an optical reflectance method of determining the degree of amorphism, surface roughness, and presence of a contaminating film on the surface of a SIMOX article. Harbeke et al. teach illuminating the SIMOX surface with light beams of three selected wavelengths: 240 nm, 320 nm, and 367 nm. The reflections of these light beams indicate reflectance changes corresponding to amorphism, surface roughness, and the presence of a surface contaminating film.

In "Advanced Methods of Ion Implant Monitoring Using Optical Dosimetry" by J. R. Golin et al., Solid State Tech., June 1985, pp. 155–163, a prior art optical dosimetry method is disclosed. The method measures the optical transmission through a photoresist-coated glass substrate that has been darkened by exposure to the implant beam. A change in the optical density is related to the implant dose. It is important to note that measurement sensitivity for this method falters in the low dose regime with low dose sensitivity of only ±10%, as indicated by the published data. What is more, since it requires special glass substrate on which the photoresist layer is deposited, silicon wafers cannot be used in this method. As such, there is questionable correlation to actual implant conditions, e.g., wafer charging or channeling effects, performed on silicon wafers through gate or screen oxides.

On the other hand, it has been discovered that, in some cases, non-destructive optical methods and apparatuses can be used to test highly doped, "opaque" silicon wafers, i.e., where silicon crystal is impregnated with high dose impurities such as phosphorous (P) or boron (B). For example, U.S. Pat. No. 5,007,741, titled "METHODS AND APPARATUS FOR DETECTING IMPURITIES IN SEMICONDUCTORS," issued to Carver et al., and assigned to AT&T Bell Laboratories of Murray Hill, N.J., U.S.A., disclosed a method for detecting small amounts of impurity, i.e., trace interstitial oxygen, in highly doped silicon wafers. The wafers have a doping concentration in excess of $1.0 \times 10^{18}$ (1E18) conductivity-determining atoms/$cm^2$. This method uses a carbon dioxide laser or a lead-salt diode laser to form a light beam having a high proportion of its power at an optical frequency capable of being absorbed by the impurity to be measured, i.e., at a single wavelength within the characteristic oxygen absorption band 8.9–9.15 microns. Using the system set up disclosed by Carver et al., small changes of reflectivity due to the presence of an interstitial impurity could be detected by comparing the light reflected from such a surface with light reflected from a semiconductor wafer having a known quantity of such impurity. However, Carver et al.'s method and system is limited to detecting presence of an impurity in highly doped silicon wafers and is incapable of measuring reflectance changes at wavelengths other than one that is within the characteristic absorption band of the impurity to be measured.

What is needed in the art is an optical reflectance system and method for high resolution non-destructive monitoring of low dose ion implantation in an accurate and reproducible manner without suffering from potential undesirable annealing effects even as semiconductor technologies continue to scale.

BRIEF SUMMARY OF THE INVENTION

It is therefore a primary object of the present invention to provide a computer-implemented reflectance method that does not suffer from undesirable annealing effects for accurate and non-destructive low dose ion implantation monitoring, the method including the steps of:

a) providing illumination at all wavelengths (wl) on a silicon or silicon oxide wafer;

b) obtaining non-implanted reflectance measurements ($R_{ref}$) of the wafer at each of the wavelengths ($R_{ref,wl}$);

c) obtaining implanted reflectance measurements ($R_{imp}$) at each of the wavelengths ($R_{imp,wl}$);

d) forming respective non-implanted and implanted reflectance values over the entire measured spectra;

e) comparing non-implanted and implanted reflectance values and determining reflectance changes; and f) determining a reflectance change index value where said reflectance change index equals $$\sum_{wl=190}^{1000} \left| \left( \frac{(R_{ref,wl} - R_{imp,wl})}{R_{ref,wl}} \right) \right|$$

such that said reflectance change index correlates to the low dose.

It is also an object of the present invention to provide a computer-implemented reflectance system and corresponding computer program product for accurate and non-destructive monitoring of low dose ion implantation, the system comprising:

a single source for providing visible and invisible lights at a substantially broad range of wavelengths (wl) on a silicon or silicon-oxide wafer;

a spectrophotometer for obtaining non-implanted reflectance measurements ($R_{ref}$) and implanted reflectance measurements ($R_{imp}$) of the wafer at each of the wavelengths, ($R_{ref,wl}$) and ($R_{imp,wl}$), respectively, and outputting those reflectance measurements; and a computer for analyzing the reflectance measurements, comprising a processor, a memory, and a computer-readable medium carrying instructions executable by the processor, the computer-executable instructions comprise:

program codes for forming respective reflectance values of the non-implanted and implanted reflectance measurements over the entire measured spectra;

program codes for comparing the respective non-implanted and implanted reflectance values and determining reflectance changes;

program codes for determining a reflectance change index value that equals $$\sum_{wl=190}^{1000} \left| \left( \frac{(R_{ref,wl} - R_{imp,wl})}{R_{ref,wl}} \right) \right|,$$

where the reflectance change index correlates to the low dose of ions implanted in the wafer; and program codes for providing a graphic user interface environment capable of displaying the reflectance change index values, the ion doses, the correlation thereof, and receiving user input.

Still further objects and advantages of the present invention will become apparent to one of ordinary skill in the art upon reading and understanding the following drawings and detailed description discussed herein. As it will be appreciated by one of ordinary skill in the art, the present invention may take various forms and may comprise various components, steps and arrangements thereof. Accordingly, the drawings are for purposes of illustrating principles and embodiments of the present invention and are not to be construed as limiting the present invention.

BRIEF DESCRIPTION OF THE DRAWINGS

FIG. 2A illustrates where the multi-point reflectance measurements are preferably taken on a wafer in accordance with an embodiment of the present invention.

FIG. 2B is a magnified view showing an exemplary arrangement of the multi-point reflectance measurements in accordance with an embodiment of the present invention.

FIG. 3A illustrates a wafer having a plurality of locations where the multi-point reflectance measurements may be taken, with a magnified view of another exemplary arrangement of the multi-point reflectance measurements, in accordance with another embodiment of the present invention.

FIG. 3B shows an exemplary map of the wafer of FIG. 3A with regions correlated to ion doses implanted in the wafer.

DETAILED DESCRIPTION OF THE INVENTION

Figure 1:
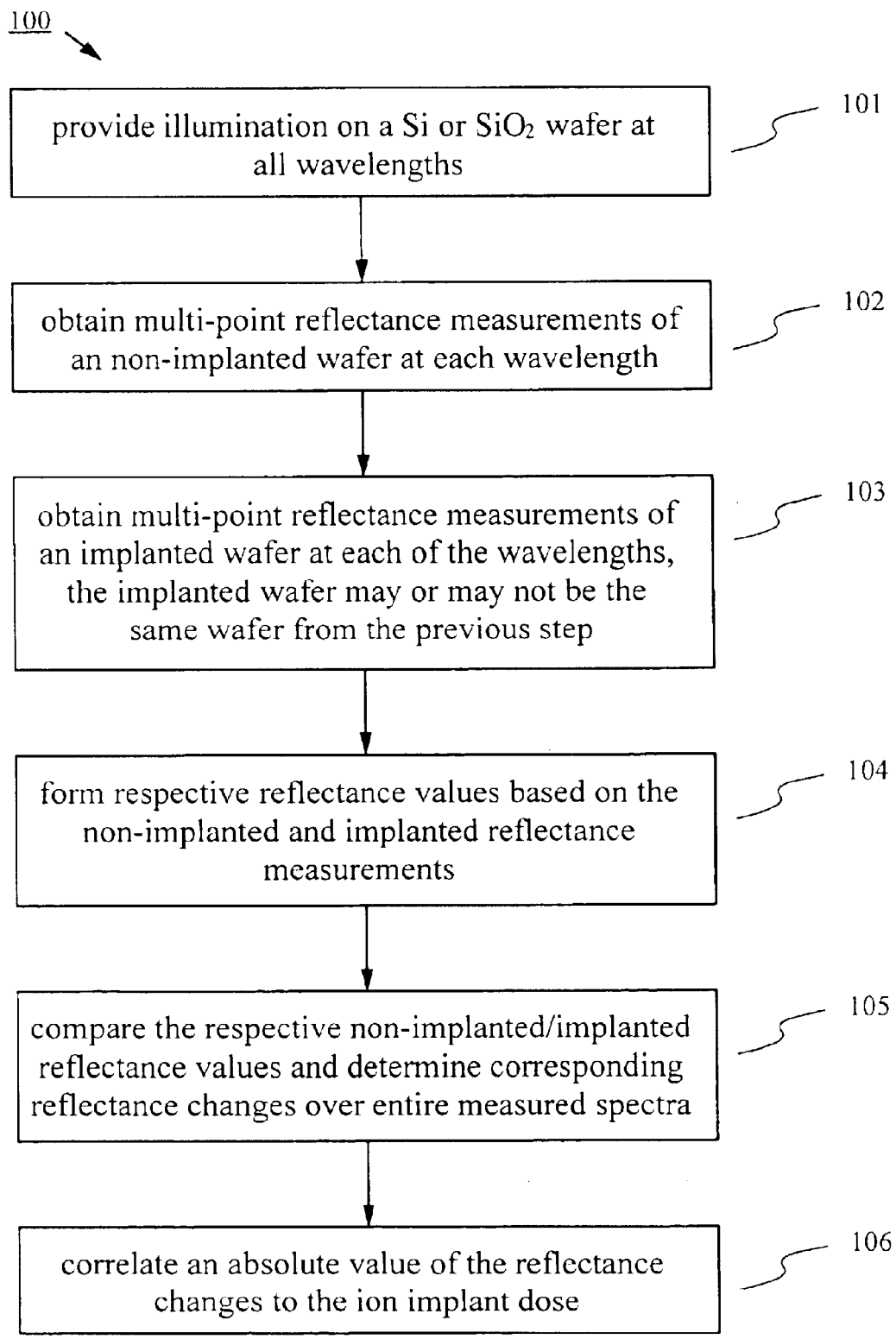
FIG. 1 is a flowchart describing a computer-implemented reflectance method for monitoring low dose ion implants according to the present invention.

In some prior art reflectance systems and methods, such as ones disclosed by Thakur et al. in U.S. Pat. No. 6,327,040, titled "REFLECTANCE METHOD FOR EVALUATING THE SURFACE CHARACTERISTICS OF OPAQUE MATERIALS" and assigned to Micron technology, Inc. of Boise, Id., U.S.A., and by Honma et al. in U.S. Pat. No. 5,796,484, titled "SYSTEM FOR DETECTING UNEVENNESS DEGREE OF SURFACE OF SEMICONDUCTOR DEVICE" and assigned to NEC Corporation of Japan, light having a wavelength of about 240 nm–500 nm is used to measure and analyze surface characteristics of a material. Bumps and other small physical features, such as hemispherical-gain (HSG) polycrystalline silicon, formed on the surface of a silicon material contribute to the surface characteristic peaks. In other words, such reflectance systems and methods measure the degree of roughness. When there are bumps or non-flat features on a surface, there will not be as much observed reflection as for a flat surface. This is essentially a scattering of the light so that a lower intensity is measured by the detector.

What is more, reflection changes due to roughness, i.e., light scattering, would be highest at shorter wavelength light, and decrease as the wavelength increases. As such, the reflectance changes due to roughness decrease monotonically with wavelength. Applicants of the present invention have observed that this is not the case for ion implantation.

The reflectance changes that we observed fluctuate in a reproducible manner as the wavelength is increased. What is more, the reflectance actually increases over certain wavelength ranges. This is very different from the prior art systems where the reflectance decreases with increased surface roughness, so the highest reflectance would be from a flat surface, i.e., surface with no roughness.

More importantly, the reflectance changes observed for ion implantation are not necessarily due to loss of light from bumps or other physical features on the surface, rather, they are associated with the slight changes in electrical/optical properties due to the ion implantation. Applicants discovered that the implanted ions, which penetrate the surface, indeed cause reflectance changes over the visible and invisible ranges. Accordingly, while the prior art systems correlate reflectance loss over a specified wavelength to roughness, the present invention correlates the absolute reflectance changes, i.e., loss and gain, over the entire visible and invisible ranges to ion implantation dose.

Several embodiments of the present invention will now be described with reference to the drawings disclosed herein. Although reflectance data for two types of wafers: bare silicon (Si) and 1000 Å silicon-oxide (SiO$_2$) with near surface doping are disclosed herein, it will be apparent to one of ordinary skill in the art that the present invention may be used to examine other types of semiconductor wafers. Similarly, although implanted wafers disclosed herein are impregnated with B at 40 keV, ranging in doses from 1.0E11 to 1.0E15, various ion implantation parameters, such as types of dopants, implant energy levels, and implant doses, may be altered without departing from the spirit and scope of the present invention.

FIG. 1 is a flowchart showing steps of an inventive reflectance method 100 for non-destructive monitoring low dose ion implants according to an embodiment of the present invention. In step 101, a silicon or silicon oxide wafer is illuminated with light in visible and invisible ranges. The illumination preferably is provided by a single source that is equally efficient at all wavelengths (wl), e.g., from about 190 nm to 1000 nm. In step 102, non-implanted reflectance measurements ($R_{ref}$) of the wafer are taken at each of the wavelengths ($R_{ref,wl}$).

In some embodiments, the implanted reflectance measurements are taken from multiple points at a location near center of the wafer 200 shown in FIG. 2A. The multiple points may be arranged as arrangement 201, shown in details in FIG. 2B, with 8 points immediately surrounding a center point at equal distance of about 1 mm. Note various distance, location, and number of the reflectance measurements taken may be implemented. For example, as shown in FIG. 3A, as little as three reflectance measurement points may be necessary for a mapped wafer 300. As shown in arrangement 301 of FIG. 3A, three measurement points are taken near a single location on the mapped wafer 300, which, as shown in FIG. 3B, can be mapped with regions 311–316 doped with various doses of ion implants.

The numbers of respective measurement points, i.e., 9 for a wafer or 3 on a mapped wafer, are estimated based on test measurements taken from a single measuring device. Multiple measurements at different locations can be used to average out noise and diminish the result of wafer placement errors. The more wafer measurement points taken, the more accurate the results are. It is anticipated, however, that the number of required measurements may be diminished and small errors created by the internal variability of the measurement system may be reduced and/or eliminated with an improved measurement system or measurement setup.

Note at each wavelength these multi-point reflectance measurements, non-implanted or implanted, are taken substantially simultaneously within seconds. The time necessary to take these measurements depends on the resolution desired, i.e., number of points per a location and/or number of locations per a wafer. For example, 50 reflectance measurements could be taken over the entire measured spectra, from about 190 nm to about 1000 nm, in less than two minutes. To make a mapping at 25 locations across wafer 300 with 3 measurement points per a location, 75 total reflectance measurements would take about 2.5 to 3 minutes.

Referring back to FIG. 1, in step 103, implanted reflectance measurements ($R_{imp}$) are taken at each of the wavelengths ($R_{imp,wl}$). In some embodiments, these implanted reflectance measurements are taken from the same wafer after the wafer is implanted with a low dose of B ions at 40 keV. This would produce a more accurate result especially in lower doses. In some embodiments, these implanted reflectance measurements are taken from a different wafer of the same material as the non-implanted wafer, in which case, the location and the arrangement of the multi-point reflectance measurements taken should closely match those taken for the non-implanted wafer, i.e., at essentially the same location with the same number and arrangement of the measurement points.

In step 104, non-implanted and implanted reflectance values are respectively formed over the entire measured spectra. If the non-implanted and implanted reflectance measurements are obtained from the same wafer, average reflectance values are formed for that wafer, before and after the ion implantation. If they are from different wafers, average reflectance values are formed respectively for the respective non-implanted wafer and implanted waver.

In step 105, non-implanted and implanted reflectance values formed in step 104 are compared and the corresponding reflectance changes over the entire measured spectra are determined. A reflectance change index is then calculated in step 106 to correlate an absolute value of the reflectance changes to the dose of ions implanted in the wafer.

An exemplary embodiment of the inventive method disclosed herein will now be described with reference to FIG. 4. In this example, ten bare Si wafers were measured before and after being implanted with B at 40 keV, ranging in doses from 1E+11 to 1E+15. Wafers were loaded essentially the same position for both before and after measurements. Each test took 9 points—one center point, and 8 points at a distance of 1 mm from the center. A control wafer having no ion implants was also included (not shown).

To monitor possible drifts (machine fluctuations) in the measurement machine, each wafer could be measured several times, e.g., 3 times before implant and 3 after implant. A reference pad, e.g., a Si pad, installed on a chuck (not shown) prior to measurements may be used to account for short term drifts in the machine, i.e., pad measurements may be used as a reference to correct machine fluctuations. An assumption can be made that any measurement taken outside of the wafer radius (from the center of a wafer) would be a measurement from the Si pad. Note the machine should be calibrated (baseline) before each set of measurements. An automatic baseline from the Si pad, for example, will suffice.

Figure 4:
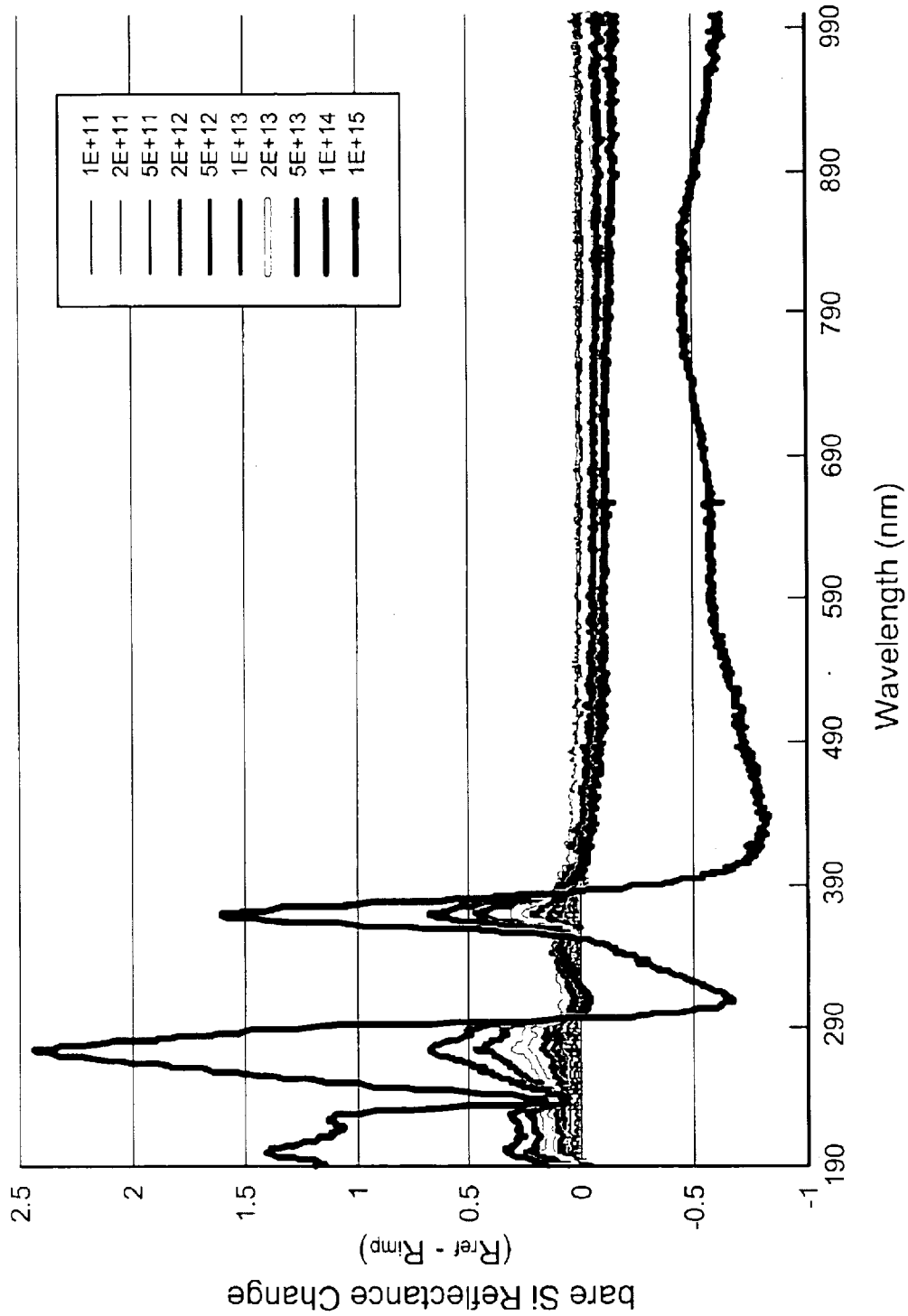
FIG. 4 is a graph showing reflectance changes of bare silicon type wafers implanted with various doses of ions over the entire measured spectra.

As shown in FIG. 4, the reflectance changes for these bare Si wafers were most notable at the reflectance peaks in the UV range, around 275 nm and 365 nm. That is, the reflectance has decreased from the pre-implant measurements to the post-implant measurements, at these wavelengths. This indicates that the greatest reflectance changes were determined by the optical properties of, and not the amount of implants in, the bare Si wafers, i.e., the present invention measures changes in the crystalline structure and not directly the amount of an impurity present within the silicon. Clearly, the wafer implanted with a 1E+15 dose of ions has undergone the largest change, while wafers implanted with ions of doses ranging from 2E+12 to 1E+14 show quite noticeable changes. Wafers implanted with lower doses ranging from 1E+11 to 5E+11 show small changes over the entire measured spectra.

Figure 5:
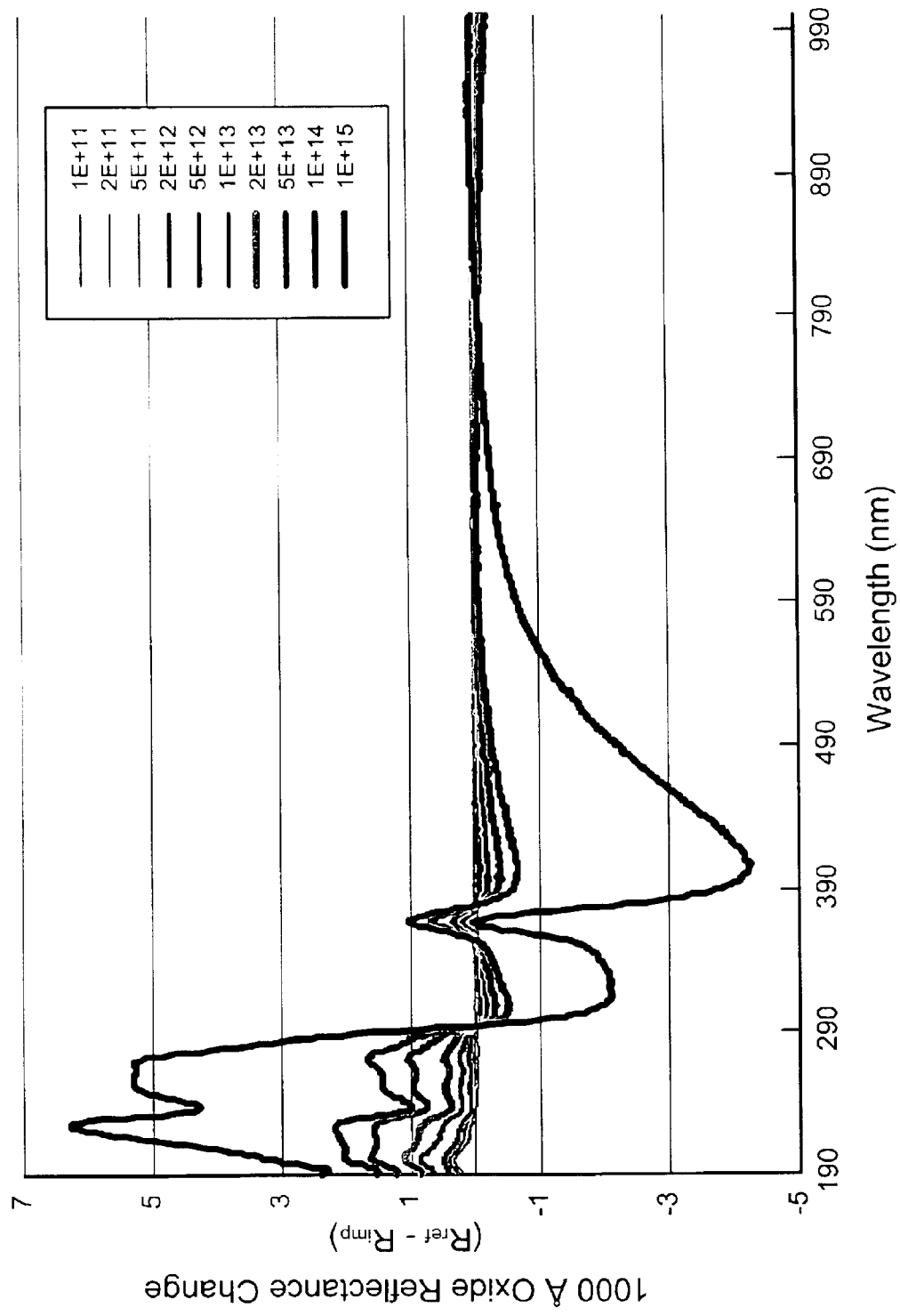
FIG. 5 is a graph showing reflectance changes of silicon oxide type wafers implanted with various doses of ions over the entire measured spectra.

In another example, ten 1000 Å $SiO_2$/Si wafers were similarly measured before and after being implanted with B at 40 keV, ranging in doses from 1E+11 to 1E+15. There is less variability and hence smaller error in bare Si measurements. However, depending on the implant energy, the effects of the implant may be more visible with an oxide layer, producing a higher reflectance change index value. As can be seen in FIG. 5, these oxide wafers show similar trends near the peaks of their respective reflectance. Again, the wafer implanted with a 1E+15 dose of ions has undergone the largest change, while wafers implanted with ions of doses ranging from 2E+12 to 1E+14 show quite noticeable changes. Wafers implanted with lower doses ranging from 1E+11 to 5E+11 show small changes over the entire measured spectra.

In both examples, pre-implant data and post-implant data were initially compared using integration, and similar calculations, around the peaks. The calculated values proved to be dependent upon the implant dose. Although the initial calculation was performed at several sets of wavelengths, the Applicants have discovered that a calculation could be done over the entire measured spectra, i.e., 190 nm to 1000 nm. That is, although the largest effect on any calculation will be around the peaks, the relative small changes at other wavelengths can also be taken into account. Accordingly, the present invention provides a reflectance change index that would best fit the data. The reflectance change index, which is a sum of the absolute values of the percent changes in reflectance at each wavelength, is defined as follows:

$$\sum_{wl=190}^{1000} \left| \left( \frac{(R_{ref,wl} - R_{imp,wl})}{R_{ref,wl}} \right) \right|$$

As discussed heretofore, these absolute reflectance changes correlate the reflectance loss and gain to ion implant dose over the entire measured spectra. The resulting reflectance change index values for the bare Si wafers of FIG. 4 and the 1000 Å oxide wafers of FIG. 5 are shown in Table 1 below.

TABLE 1

Reflectance Change Index

| Ion Implant Dose | Bare Si Wafers | 1000 Å Oxide Wafers |
| --- | --- | --- |
| 1.00E+11 | 0.15849 | 0.46415 |
| 2.00E+11 | 0.207 | 0.68693 |
| 5.00E+11 | 0.2669 | 0.84507 |
| 2.00E+12 | 0.36807 | 1.29232 |
| 5.00E+12 | 0.51182 | 1.80894 |
| 1.00E+13 | 0.68986 | 2.56799 |
| 2.00E+13 | 1.00656 | 3.78737 |
| 5.00E+13 | 1.71488 | 6.71811 |
| 1.00E+14 | 2.7998 | 10.81677 |
| 1.00E+15 | 12.77629 | 46.18329 |

Figure 6:
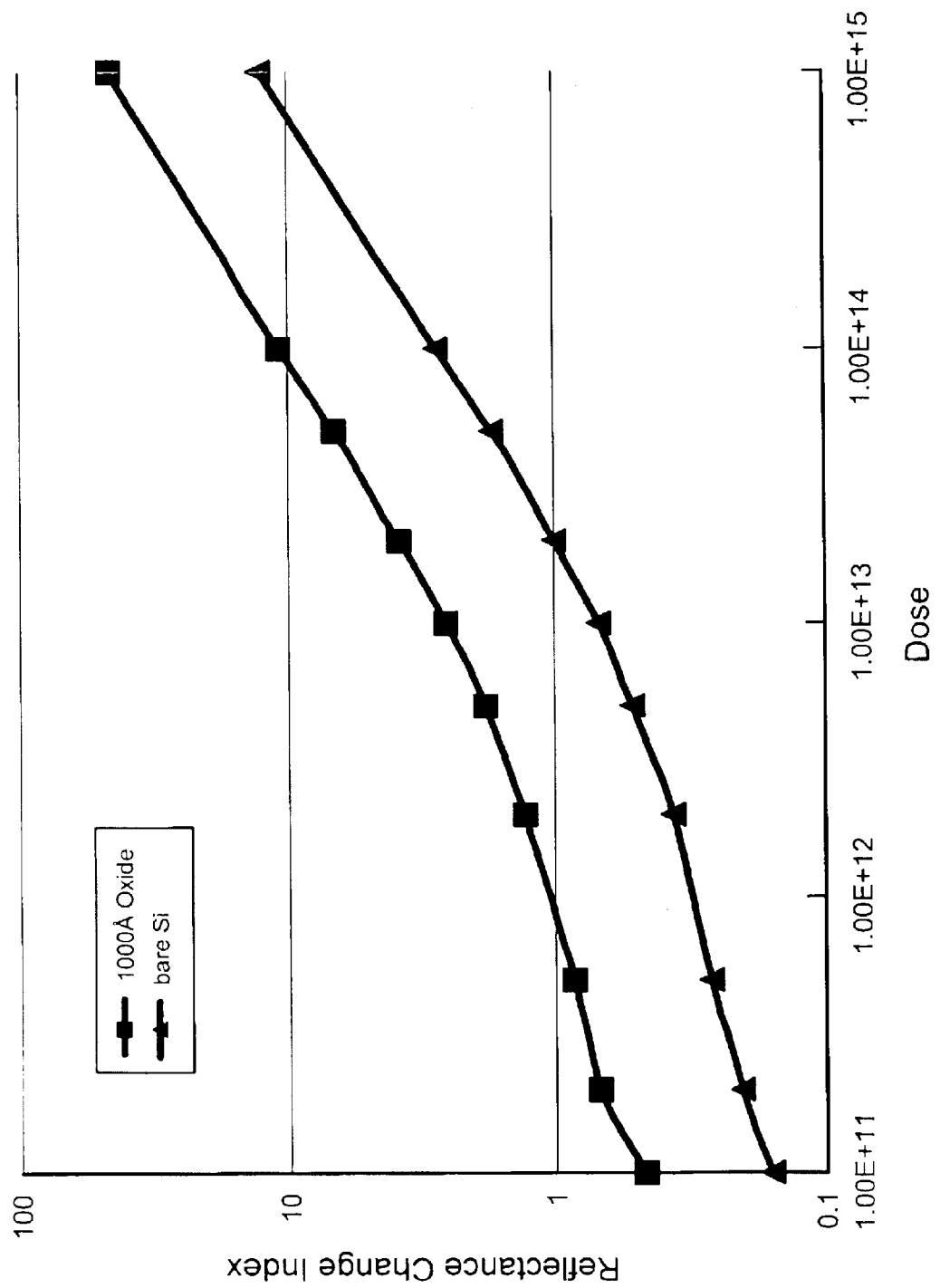
FIG. 6 is a graph illustrating the respective correlations between reflectance changes and ion doses implanted in the wafers of FIGS. 4 and 5.

Referring to FIG. 6, the bare Si wafers and the 1000 Å oxide wafers follow the same trend with the 1000 Å oxide wafers displaying a higher level of reflectance change. This is because the damage is more "visible" through the oxide layer than through silicon. Note for B at 40 keV, the range in implant depth is around 3000 Å for both silicon and oxide. The peak is about 1500 Å for silicon and 1700 Å for oxide. As such, for bare Si and 1000 Å oxide wafers, the peak is within the silicon and the range extends well into the silicon. For a silicon wafer with 3000 Å of oxide, the extent of the implant range would be near the oxide/silicon interface and the peak damage would occur within the oxide layer, as opposed to within silicon. Other factors, such as non-uniformity of $SiO_2$ film thickness, may also affect the result.

In a preferred embodiment, the inventive method is implemented in a reflectance spectrophotometric system such as one described in details in U.S. Pat. No. 5,880,831, which is hereby incorporated herein in its entirety, titled "REFLECTANCE SPECTROPHOTOMETRIC APPARATUS WITH OPTICAL RELAY," issued to Buermann et al., and assigned to the assignee of the present application, n & k Technology, Inc. of Santa Clara, Calif., U.S.A. For theoretical principles of the reflectance system, readers are referred to U.S. Pat. No. 4,905,170, co-developed by the co-inventor of the present application, issued to Forouhi et al. and titled "METHOD AND APPARATUS OF DETERMINING OPTICAL CONSTANTS OF AMORPHOUS SEMICONDUCTORS AND DIELECTRICS," which is hereby incorporated herein in its entirety.

Figure 7:
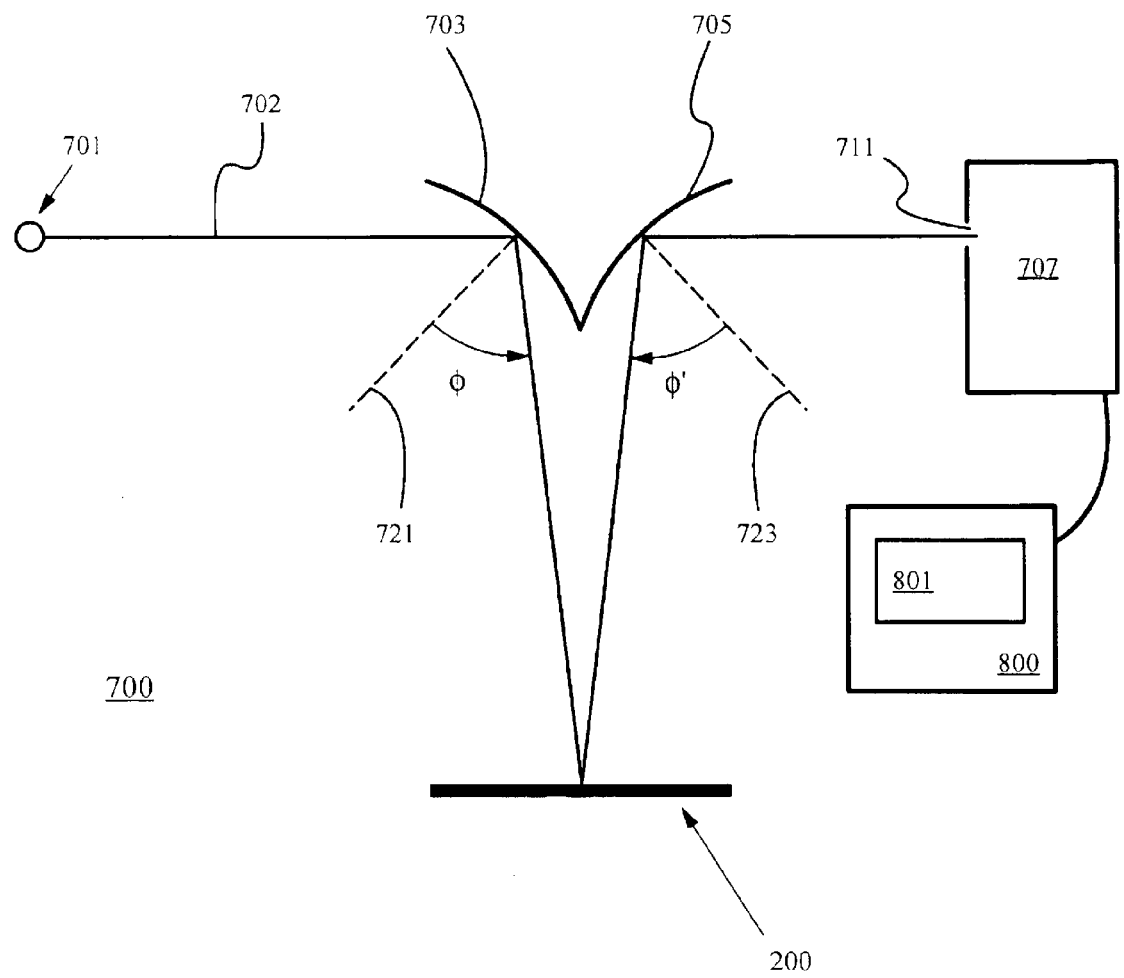
FIG. 7 illustrates a computer-implemented reflectance system having a computing device in which the present invention may be embodied.

As shown in FIG. 7, the present invention may be embodied in system 700 comprising a light source 701, a spectrophotometer 707, and a computer 800. The light source 701 emits light beam 702 having a broad spectrum ranging from about 190 nm to about 1000 nm. Beam 702 is reflected and focused by source mirror 703 onto wafer 200 with an angle $\phi$ with respect to normal 721. Beam 702 is reflected from wafer 200 and strikes detector mirror 705 with an angle $\phi'$ with respect to normal 723. Mirrors 703 and 705 may or may not be identical, but they must serve the dual role of both reflecting and focusing beam 702. Mirrors 703 and 705 comprise an optical relay for directing light from source 701 to wafer 200 and then from wafer 200 to slit 711 of the spectrophotometer 707.

The spectrophotometer 707 measures the spectrum of beam 702 and obtains non-implanted reflectance measurements ($R_{ref}$) and implanted reflectance measurements ($R_{imp}$) of wafer 200. It is important to note that system 700 is capable of measuring the reflectance spectrum of a sample over wavelengths in the range from about 190 nm to 1000 nm without chromatic aberration. That is, the reflectance system where the present invention may be embodied should be efficient at all wavelengths so that measured spectra are free from distortion. Accordingly, although the reflectance system of Buermann et al. is preferably utilized herein, any high resolution reflectance systems that are capable of providing accurate and reproducible reflectance measurements at wavelengths ranging from about 190 nm to 1000 nm, may be utilized to implement the present invention. Thus, system 700 is intended for illustrative purposes only and not to be construed as limiting the present invention.

Non-implanted reflectance measurements ($R_{ref}$) and implanted reflectance measurements ($R_{imp}$) of wafer 200 are respectively obtained at each of the wavelengths, ($R_{ref,wl}$) and ($R_{imp,wl}$), and transmitted to computer 800 for analysis. The computer 800 includes a processor, a memory, a permanent storage, a display, a mouse, and a keyboard, all of which are not shown, and a software tool 801, which will now be described in details with reference to FIGS. 8A and 8B.

The inventive software tool 801 enables users of system 700 to compare sample wafers with stored data collected in accordance with the inventive method disclosed herein. For example, with software tool 801, a user of the computer-implemented system 700 can compare samples of bare Si and/or 1000 Å $SiO_2$/Si wafers implanted with B at 40 keV to stored data collected from those bare Si and 1000 Å $SiO_2$/Si wafers described herein with reference to FIGS. 4–6.

According to an aspect of the present invention, the software tool 801 is capable of forming reflectance values based on non-implanted and/or implanted reflectance measurements taken over a substantially broad range of wavelengths, comparing those reflectance values, determining reflectance changes and corresponding reflectance change index values, and correlating the reflectance change index to ion implant doses.

Figure 8A:
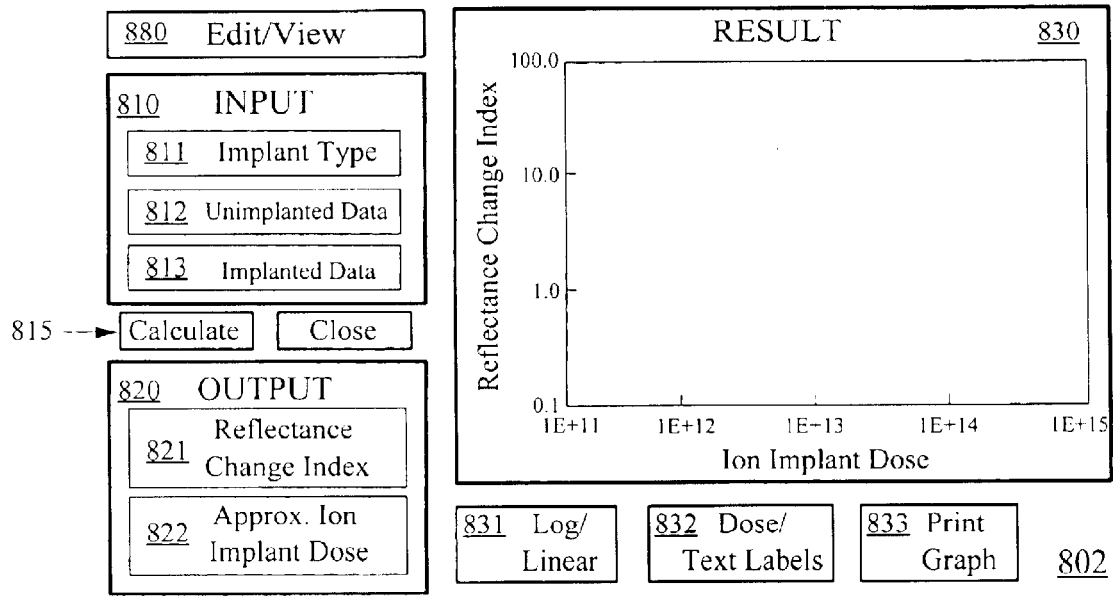
FIGS. 8A and 8B illustrate an exemplary graphic user interface of the computing device in accordance with an embodiment of the present invention.
Figure 8B:
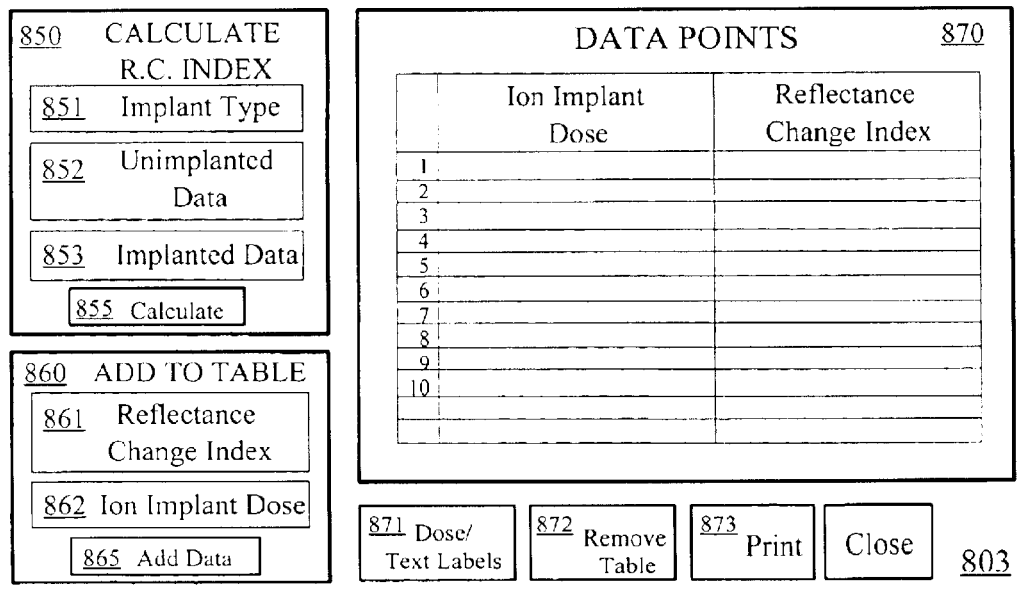

The software tool 801 further provides a user-friendly graphic interface having at least a main interface 802 and an edit data points interface 803, as respectively shown in FIGS. 8A and 8B. Referring to FIG. 8A, the main interface 802 comprises a view/edit button 880, an input window 810, an output window 820, and a result window 830. The user presses the edit/view button 880 to view or edit a correlation between implant dose and reflectance change value. The main interface 802 also provides a plurality of switches and buttons, including a log/linear switch 831, a dose/text labels switch 832, a print graph button 833, a calculate button 803, and a close button. The log/linear switch 831 allows the user to switch y-axis of a graph in the result window 830 from log to linear plot. The dose/text labels switch 832 allows the user to switch x-axis of the graph in the result window 830 from log to linear plot and/or change the x labels from numeric (scientific) to text.

The input window 810 provides user access and enables the user to select input parameters from implant type menu 811, non-implanted reflectance measurements menu 812, and implanted reflectance measurements menu 813. For example, the user selects input parameters for a single wafer, as measured using system 700, taken both before and after ion implantation. In response to the user pressing the calculate button 815, the software tool 801 calculates the corresponding reflectance change index based on the input parameters selected in the input window 810, interpolates over the stored implant type values to estimate current ion implant dose, and displays the respective resulting values in blocks 821 and 822. The interpolation, i.e., correlation between the reflectance change index and ion implant dose for the selected wafer type, as well as the determined values for the measured wafer, appears in the result window 830. The user then prints a desired graph via the print button 833.

With software tool 801, the user can create new correlations for ion implant with other species, energies, or wafer types. To create a new correlation, the user provides non-implanted and implanted reflectance measurements as well as the implant dose for each set of the measurements. Referring to FIG. 8B, the edit data points interface 803 comprises a calculate window 850, an add data window 860, a data points window 870, and a plurality of switches and buttons including a dose/text labels switch 871, a remove table button 872, a print button 873, and a close button.

Similar to their counterparts in the main interface 802, implant type menu 851, non-implanted data menu 852, and implanted data menu 853 enable the user to select input parameters, and calculate button 855 enables the user to find a corresponding reflectance change index. Determined values thereof are then displayed in the data points window 870. The software tool 801 enables the user to create a correlation, i.e., to add a data point, (ion implant dose, reflectance change index), via blocks 861, 862 and add data button 865, to the data points table shown in the data points window 870. Note multiple reflectance change values are acceptable for a single dose. When the software tool 801 interpolates, it uses an average of these values for the single dose. A data point displayed in the data points window 870 can be deleted by selecting the row of the data point to be deleted with the mouse and pressing the "Delete" or "Backspace" key on the keyboard of computer 800.

The dose/text labels switch 871 changes dose values (numeric) into names of the corresponding measurements (text) so that the reflectance change values can be associated with names such as "wafer A", "wafer B", "wafer C", "low dose", "high dose", etc. The current data points table displayed in the data points window 870 can be printed by pressing the print button 873 and/or deleted/cleared entirely by pressing the remove table button 872. Alternatively, a new table (correlation) of data points can be created by selecting "New Type" (not shown) from the implant type menu 851 and giving it a unique name.

According to an aspect of the present invention, the inventive software tool 801 is embodied in a computer program product residing in the computer-implemented reflectance system 700 for implementing the inventive method 100 for non-destructive monitoring low dose ion implantation. The computer program product comprises a computer-readable medium carrying computer instructions executable by the processor of computer 800. The computer-executable instructions comprise 1) program codes for forming reflectance values based on non-implanted reflectance measurements and implanted reflectance measurements taken over the entire measured spectra from about 190 nm to about 1000 nm wavelengths; 2) program codes for comparing the non-implanted and implanted reflectance values and for determining absolute reflectance changes and deriving a reflectance change index value thereof; and 4) program codes for providing a graphic user interface environment including the main interface 802 and the edit data points interface 803.

Although the present invention and its advantages have been described in detail, it should be understood that various changes, substitutions, and alternations could be made and/or implemented without departing from the principles and the scope of the invention. Accordingly, the scope of the present invention should be determined by the following claims and their legal equivalents.

We claim:

1. A computer-implemented reflectance method for non-destructive monitoring low dose ion implantation in a material, said method comprising the steps of:
   a) providing illumination on a first sample of said material, wherein said material comprises silicon or silicon-oxide wafers and said first sample is a sample wafer thereof, and wherein said illumination spans a substantially broad range of wavelengths (wl);
   b) obtaining non-implanted reflectance measurements ($R_{ref}$) of said first sample at each of said wavelengths ($R_{ref,wl}$);
   c) implanting said first sample with said low dose of ions and obtaining implanted reflectance measurements ($R_{imp,wl}$) of said first sample at each of said wavelengths ($R_{imp,wl}$) wherein said non-implanted reflectance measurements are substantially simultaneously obtained at a location near center of said first sample and said implanted reflectance measurements are substantially simultaneously obtained at essentially same location of said first sample;
   d) forming reflectance values over said wavelengths based on said non-implanted and implanted reflectance measurements;
   e) comparing non-implanted and implanted reflectance values and determining reflectance changes; and
   f) correlating an absolute value of said reflectance changes to said low dose including determining a reflectance change index value where said reflectance change index equals $$\sum_{wl=190}^{1000} \left| \left( \frac{(R_{ref,wl} - R_{imp,wl})}{R_{ref,wl}} \right) \right|$$

such that said reflectance change index is directly related to said low dose.

2. A non-destructive method of monitoring low dose ion implantation in a material, said method comprising the steps of:
   a) providing illumination on a first sample of said material, wherein said material comprises silicon or silicon-oxide wafers and said first sample is a sample wafer thereof, and wherein said illumination spans a substantially broad range of wavelengths (wl);
   b) obtaining non-implanted reflectance measurements ($R_{ref}$) of said first sample at each of said wavelengths ($R_{ref,wl}$);
   c) implanting said first sample with said low dose of ions and obtaining implanted reflectance measurements ($R_{imp}$) of said first sample at each of said wavelengths ($R_{imp,wl}$), wherein said non-implanted reflectance measurements are substantially simultaneously obtained at a plurality of locations of said first sample and said implanted reflectance measurements are substantially simultaneously obtained at essentially same locations of said first sample;

d) forming reflectance values over said wavelengths based on said non-implanted and implanted reflectance measurements;

e) comparing non-implanted and implanted reflectance values and determining reflectance changes; and f) determining a reflectance change index value where said reflectance change index equals $$\sum_{wl=190}^{1000} \left| \left( \frac{(R_{ref,wl} - R_{imp,wl})}{R_{ref,wl}} \right) \right|$$

such that said reflectance change index is directly related to said low dose.

3. The method of claim 2, wherein each location comprises at least three points arranged to be at equal distance from each other.

4. The method of claim 3, wherein said distance is about 1 mm.

5. The method of claim 1, wherein said location comprises at least three points arranged to be at equal distance from each other.

6. The method of claim 5, wherein said distance is about 1 mm.

7. The method of claim 1, wherein said location comprises a center point and eight points surrounding said center point at equal distance.

8. The method of claim 7, wherein said distance is about 1 mm.

9. The method of claim 3, wherein each location comprises a center point and eight points surrounding said center point at equal distance.

10. A non-destructive method of monitoring low dose ion implantation in a material, said method comprising the steps of:

a) providing illumination on a first sample of said material, wherein said material comprises silicon or silicon-oxide wafers and said first sample is a sample wafer thereof, and wherein said illumination spans a substantially broad range of wavelengths (wl);

b) obtaining non-implanted reflectance measurements ($R_{ref}$) of said first sample at each of said wavelengths ($R_{ref,wl}$);

c) implanting said first sample with said low dose of ions and obtaining implanted reflectance measurements ($R_{imp}$) of said first sample at each of said wavelengths ($R_{imp,wl}$);

d) forming reflectance values over said wavelengths based on said non-implanted and implanted reflectance measurements, wherein said $R_{ref}$ reflectance values are average reflectance values of said first sample before said low dose ion implantation and said $R_{imp}$ reflectance values are average reflectance values of said first sample after said low dose ion implantation;

e) comparing non-implanted and implanted reflectance values and determining reflectance changes; and f) determining a reflectance change index value where said reflectance change index equals $$\sum_{wl=190}^{1000} \left| \left( \frac{(R_{ref,wl} - R_{imp,wl})}{R_{ref,wl}} \right) \right|$$

such that said reflectance change index is directly related to said low dose.

11. The method of claim 10, wherein said non-implanted reflectance measurements are substantially simultaneously obtained at one or more locations of said first sample and said implanted reflectance measurements are substantially simultaneously obtained at essentially same one or more locations of said first sample.

12. A non-destructive method of monitoring low dose ion implantation in a material, said method comprising the steps of:

a) providing illumination on a first sample of said material, wherein said material comprises silicon or silicon-oxide wafers and said first sample is a sample wafer thereof, and wherein said illumination spans a substantially broad range of wavelengths (wl);

b) obtaining non-implanted reflectance measurements ($R_{ref}$) of said first sample at each of said wavelengths ($R_{ref,wl}$);

c) obtaining implanted reflectance measurements ($R_{imp}$) of a second sample of said material at each of said wavelengths ($R_{imp,wl}$), said second sample being implanted with said low dose of ions;

d) forming reflectance values over said wavelengths based on said non-implanted and implanted reflectance measurements, wherein said $R_{ref}$ reflectance values are average reflectance values of said first sample and said $R_{imp}$ reflectance values are average reflectance values of said second sample;

e) comparing non-implanted and implanted reflectance values and determining reflectance changes; and f) determining a reflectance change index value where said reflectance change index equals $$\sum_{wl=190}^{1000} \left| \left( \frac{(R_{ref,wl} - R_{imp,wl})}{R_{ref,wl}} \right) \right|$$

such that said reflectance change index is directly related to said low dose.

13. The method of claim 12, wherein said non-implanted reflectance measurements are obtained at a first location near center of said first sample and said implanted reflectance measurements are obtained at a second location near center of said second sample, and wherein said first location is essentially same as said second location.

14. The method of claim 13, wherein each of said first and second locations comprises at least three points arranged to be at equal distance of about 1 mm from each other.

15. The method of claim 13, wherein each of said first and second locations comprises a center point and eight points surrounding said center point at equal distance of about 1 mm.

16. The method of claim 12, wherein said non-implanted reflectance measurements are obtained at a plurality of locations of said first sample and said implanted reflectance measurements are obtained at a plurality of locations of said second sample.

17. The method of claim 1, wherein said ion implantation utilizing boron (B) ions.

18. The method of claim 1, wherein said illumination includes radiation frequencies in visible and invisible electromagnetic spectra.

19. The method of claim 1, wherein said range is about 190 nm to 1000 nm.

20. The method of claim 1, wherein said low dose is about 1.00E+11 to 1.00E+15.

21. A system for non-destructive monitoring low dose ion implantation in a material, comprising:

a light source means for providing illumination on a first sample of said material wherein said material comprises silicon or silicon-oxide wafers and wherein said illumination spans a substantially broad range of wavelengths (wl);

an optical sensing means optically coupled to said light source means for obtaining non-implanted reflectance measurements ($R_{ref}$) and implanted reflectance measurements ($R_{imp}$) of said sample at each of said wavelengths, ($R_{ref,wl}$) and ($R_{imp,wl}$), respectively, and transmitting reflectance measurements obtained thereof; and a computing means operatively coupled to said optical sensing means for analyzing said transmitted reflectance measurements, comprising:

means for forming respective reflectance values over said wavelengths based on said non-implanted reflectance measurements and implanted reflectance measurements;

means for comparing said non-implanted and implanted reflectance values and determining reflectance changes;

means for determining a reflectance change index value, said reflectance change index correlating an absolute value of said reflectance changes to said low dose; and means for providing said reflectance change index value to a user and receiving user input via a graphic user interface wherein said graphic user interface comprises an input area, an output area, and a result area, wherein said input area is configured to include placements for implant type, said non-implanted reflectance measurements, and said implanted reflectance measurements, wherein said output area is configured to include placements for said reflectance change index and said low dose, and wherein said result area is configured to display a graphical result showing a relationship between said reflectance change index and said low dose.

22. The system of claim 21, wherein said reflectance change index value equals $$\sum_{wl=190}^{1000} \left| \left( \frac{(R_{ref,wl} - R_{imp,wl})}{R_{ref,wl}} \right) \right|.$$

23. The system of claim 21, wherein said light source means is capable of providing radiation frequencies in visible and invisible electromagnetic spectra.

24. The system of claim 21, wherein said range is about 190 nm to 1000 nm.

25. The system of claim 21, wherein said low dose is about 1.00E+11 to 1.00E+15.

26. The system of claim 21, wherein said implanted reflectance measurements are obtained from a second sample of said material wherein said computing means further comprising a storing means for storing said non-implanted reflectance measurements of said first sample.

27. The system of claim 21, wherein said computing means further comprising:

a storing means for storing said non-implanted reflectance measurements and said implanted reflectance measurements.

28. The system of claim 21, wherein said user input comprises ion implant types and ion implant doses.

29. A computer system programmed to perform the method steps of claim 1.

30. A computer program product embodied in a reflectance system for implementing a method for non-destructive monitoring low dose ion implantation in a first wafer, the reflectance system comprises a light source means for providing visible and invisible light on said wafer at a substantially broad range of wavelengths (wl) and an optical sensing means for obtaining non-implanted and implanted reflectance measurements of said wafer at each of said wavelengths, ($R_{ref,wl}$) and ($R_{imp,wl}$), respectively, the computer program product comprising:

a computer-readable medium carrying computer-executable instructions for implementing the method wherein the computer-executable instructions comprise:

program code means for forming respective reflectance values over said wavelengths based on said non-implanted reflectance measurements and implanted reflectance measurements;

program code means for comparing said non-implanted and implanted reflectance values and determining reflectance changes;

program code means for determining a reflectance change index value, said reflectance change index correlating an absolute value of said reflectance changes to said low dose; and program code means for providing a graphic user interface environment to display said reflectance change index value and receive user input; wherein said graphic user interface environment comprises an input area, an output area, and a result area, wherein said input area is configured to include placements for implant type, said non-implanted reflectance measurements, and said implanted reflectance measurements, wherein said output area is configured to include placements for said reflectance change index and said low dose, and wherein said result area is configured to display a graphical result showing a relationship between said reflectance change index and said low dose.

31. The computer program product of claim 30, wherein said reflectance change index value equals $$\sum_{wl=190}^{1000} \left| \left( \frac{(R_{ref,wl} - R_{imp,wl})}{R_{ref,wl}} \right) \right|.$$

32. The computer program product of claim 30, wherein said first wafer is a silicon or silicon-oxide wafer.

33. The computer program product of claim 30, wherein said implanted reflectance measurements are obtained from a second wafer made of same material of said first wafer.

34. The computer program product of claim 30, wherein said user input includes ion implant types and ion implant doses.

35. The method of claim 11, wherein each location comprises three or more points arranged to be at equal distance from each other.

36. The computer program product of claim 30, wherein said graphic user interface environment further comprises a log/linear switch, a dose/text labels switch, a calculate button, a print button, and a close button.

37. The computer program product of claim 30, wherein said graphic user interface environment further comprises a calculate area, an add area, and a table area, wherein said calculate area is configured to calculate said reflectance change index, wherein said add area is configured to add said reflectance change index and said low dose to a table, and wherein said table area is configured to list said table.

38. The computer program product of claim 37, wherein said graphic user interface environment further comprises a dose/text labels switch, a calculate button, an add button, a remove button, a print button, and a close button.

* * * * *